United States Patent
Ni et al.

(10) Patent No.: US 11,191,728 B2
(45) Date of Patent: Dec. 7, 2021

(54) METHOD OF PREPARING DEGRADABLE AND ENVIRONMENT RESPONSIVE COMPOSITE MICROGELS

(71) Applicant: JIANGNAN UNIVERSITY, Jiangsu (CN)

(72) Inventors: Caihua Ni, Jiangsu (CN); Zhenle Tian, Jiangsu (CN); Gang Wang, Jiangsu (CN); Liping Zhang, Jiangsu (CN); Ren Liu, Jiangsu (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 30 days.

(21) Appl. No.: 16/928,186

(22) Filed: Jul. 14, 2020

(65) Prior Publication Data

US 2021/0299049 A1 Sep. 30, 2021

(30) Foreign Application Priority Data

Mar. 31, 2020 (CN) .......................... 202010243200.5

(51) Int. Cl.
  *A61K 31/704* (2006.01)
  *A61K 9/19* (2006.01)
  *C08G 63/06* (2006.01)
  *C08J 3/14* (2006.01)
  *C08J 3/075* (2006.01)

(52) U.S. Cl.
  CPC .............. *A61K 9/19* (2013.01); *A61K 31/704* (2013.01); *C08G 63/06* (2013.01); *C08J 3/075* (2013.01); *C08J 3/14* (2013.01); *C08J 2367/04* (2013.01)

(58) Field of Classification Search
  CPC .... A61K 31/704; A61K 31/7034; A61K 9/19; C08J 3/075
  USPC .......................................................... 514/34
  See application file for complete search history.

(56) References Cited

U.S. PATENT DOCUMENTS

2020/0392289 A1* 12/2020 Yin ...................... A61K 33/243

FOREIGN PATENT DOCUMENTS

| CN | 104788689 A | 7/2015 |
|---|---|---|
| GN | 104311821 A | 1/2015 |
| GN | 104491871 A | 4/2015 |
| GN | 104644559 A | 5/2015 |

* cited by examiner

*Primary Examiner* — Shaojia A Jiang
*Assistant Examiner* — Everett White
(74) *Attorney, Agent, or Firm* — Enshan Hong; MagStone Law, LLP

(57) ABSTRACT

A method of preparing degradable and environment responsive composite microgels, belonging to polymer material synthesis and biomaterial technology fields. Firstly, a copolymer of L-malic acid and 6-hydroxyhexanoate is prepared; then, N,N,N',N'-tetramethyl cystamine is prepared. The copolymer and N,N,N',N'-tetramethyl cystamine are mixed in an organic solvent to form a mixed solution which is added into excess distilled water to produce composite microgels. The microgels have advantages of mild preparing conditions, fast reaction speed without catalysts, no impurity remained, and controllable degradation rate. The microgels can load anticancer drug doxorubicin hydrochloride, showing environment responsive controlled release due to introduction of carboxyl groups and disulfide bonds.

8 Claims, 4 Drawing Sheets

METHOD OF PREPARING DEGRADABLE AND ENVIRONMENT RESPONSIVE COMPOSITE MICROGELS

RELATED APPLICATIONS

This application claims the priority from China Patent Application Serial Number CN202010243200.5, filed on Mar. 31, 2020, the content of which is incorporated here by reference.

BACKGROUND OF THE INVENTION

1. Technical Field

The invention relates to a method of preparing degradable and environment responsive composite microgels, which belongs to the field of polymer material synthesis and biomaterials technology.

2. Background of the Invention

Currently, chemotherapy is an important method to treat cancer, but common chemotherapy has many defects. Anticancer drugs not only kill cancer cells, but also have serious side effects to normal cells. Nano drug delivery systems have brought prospects for cancer treatments in recent years. Nano system s can enhance the permeability and retention (EPR) effect, avoiding recognition and capture of reticular inner cortex systems of human body, playing a "invisible" role, extending the circulation time of drug carrier systems in bloods, and improve the bioavailability of drugs.

The environment of tumor tissues are different from those of normal cells. The concentration of glutathione (GSH) in tumor cells is 0.5-10 mM, while the concentration of GSH in extracellular is only 2-20 μM. Glutathione is a tripeptide molecule containing sulfhydryl group. It is an important reductant in biochemical reaction, which can reduce disulfide bonds. In addition, the environment of tumor tissues is weakly acidic. The pH in endosome is 5.0~6.5, and the pH in lysozyme body is 4.5~5.0. Therefore, target controlled drug release can be achieved by designing environment responsive drug carriers, based on the difference of pH and reduction conditions between tumor tissues and the normal cells.

Biomedical materials need good biocompatibility and biodegradability. Poly (L-malic acid) has good biocompatibility and biodegradability. Its degradation products can be involved in the tricarboxylic acid cycle in vivo and be absorbed by organisms.

However, the degradation rate of poly (L-malic acid) is too fast and the degradation products are too acidic, which limits its application as drug delivery carrier. 6-hydroxycaproic acid has six carbon atoms in the molecule and can be used to prepare polycaprolactone which is a kind of synthetic polyester biopolymer. It has good biocompatibility, good drug compatibility, and slow degradation rate. Polycaprolactone is a satisfactory drug slow release.

Polyelectrolyte composite microgels are formed by electrostatic interactions between two oppositely charged components. One of the outstanding advantages of such microgels is that they can be used to load electrically charged drugs, genes or enzymes. Additionally, polyelectrolyte composite microgels can be prepared under mild conditions without catalysts, showing fast reaction speed, complete reaction, and no residual monomer impurities.

SUMMARY OF THE INVENTION

In order to slow down the degradation rate of poly(L-malic acid), reduce the acidity of the degradation products, and enhance environmental responsive controlled release, this invention has prepared degradable and environment responsive composite microgels. The microgels are used as carriers of anticancer drugs for controlled release by environmental stimulus.

The invention aims to provide a preparation method of degradable and environmental responsive composite microgels. Firstly, the copolymers of L-malic acid and 6-hydroxyhexanoate are prepared as the main component, the degradation rate of the copolymers can be controlled by adjusting the ratio of L-malic acid to 6-hydroxycaproic acid; then, Then, N,N,N',N'-tetramethyl cystamine is synthesized through methylation of cystamine; a composite microgel with degradable and environmental responsive properties is prepared by complexmation of the copolymer with N,N,N', N'-tetramethyl cystamine. The preparation steps are as follows:

Step (1): adding L-malic acid, 6-hydroxyhexanoic acid and catalyst into a reactor to mix evenly, connecting a condenser tube and water separation device, raising temperature to 85° C. in an oil bath, reacting for 2 h, then, raising the temperature to 140° C. for further reaction 12 h under a reduced pressure of 8-10 kpa, to obtain a copolymer of L-malic acid and 6-hydroxyhexanoic acid;

Step (2): mixing cystamine hydrochloride, sodium hydroxide solution with 25 wt % of concentration and methanol, stirring at room temperature for 0.5 h, adding iodomethane slowly under dark conditions, reacting at 25° C. for 9 h, extracting with an organic solvent, separating the organic layer, washing the organic layer by deionized water for three times, removing the organic solvent by vacuum distillation to obtain N,N,N',N'-tetramethyl cystamine;

Step (3): preparing a copolymer solution with 15 wt % of concentration in N, N-dimethylformamide; preparing N,N, N',N'-tetramethyl cystamine solution with 15 wt % of concentration in tetrahydrofuran; mixing the two solutions, then slowly dropping the mixed solutions into excess distilled water under stirring for 8 h, transferring the mixture into a dialysis bag with cutoff molecular weight of 3500, dialysing against deionized water at room temperature for 72 h; finally, a degradable and environmental responsive composite microgel is obtained after freeze-drying.

In step 1, the molar ratio of L-malic acid and 6-hydroxyhexanoic acid is 8:1~3:1.

In step (1), the catalyst is p-toluenesulfonic acid which accounts for 1.8-4.2 wt % of the total weight of L-malic acid and 6-hydroxyhexanoic acid.

In step (2), cystamine hydrochloride is 22.5 g, sodium hydroxide solution with 25 W % concentration is 100 mL, and methanol is 20 ml; the molar ratio of cystamine hydrochloride to iodomethane is 1:4.

In step (2), the organic solvent is any one of trichloromethane, dichloromethane, ethyl acetate or ether.

In step (3), the volume ratio of the copolymer solution to N,N,N',N'-tetramethyl cystamine solution is 8:1~15:1.

In step (3), the volume of distilled water is 11~25 times of the total volume of the copolymer solution and N,N,N', N'-tetramethyl cystamine solution.

Another purpose of the invention is to provide the application of the degradable and environmental responsive composite microgels, the microgels and doxorubicin hydrochloride are added to N,N-dimethylformamide solvent, reacting for 12 h at room temperature, transferring the solution into a dialysis bag for dialyzing at room temperature for 16 h against deionized water, then freeze-drying to obtain dried drug loaded nanomicelles; the dried drug loaded microgels are dissolved in deionized water to make a solution with a concentration of 1 mg/mL; 2 mL of the solution is put into a dialysis bag, the drug release is carried out at 37° C. in a phosphoric acid buffer solution with various pHs and glutathione concentrations. Further, the pH of the phosphate buffer solution is 5~7.4.

The invention has the advantages of:

(1) Mild preparing conditions, fast reaction speed, no impurity remained, and controllable degradation rate. The microgels can load doxorubicin, showing environmental responsiveness-controlled release due to introduction of carboxyl groups and disulfide bonds.

(2) The copolymers are prepared using L-malic acid and 6-hydroxycaproic acid, the degradation rate of the copolymers can be controlled by adjusting the monomer feeding ratio. The acidity of copolymer hydrolysates is lower than that of pure poly(L-malic acid) hydrolysate, which solves the problems of fast degradation of poly(L-malic acid) and strong acidity of the degraded products, making controllable degradation rate of the composite microgel. In addition, 6-hydroxy hexanoate has 6 carbon atoms and has a certain hydrophobicity, which is more conducive for drug loading and slow release.

(3) using methyl cystamine as a complex agent, the primary amine group in cystamine has been converted into tertiary amine group, which enhances its ability to complex with carboxyl group in the copolymer, making the composite microgels more stable, and is more conducive to the controlled drug release.

(4) Cysteamine molecules contain disulfide bonds in the structures. They show reductive responsiveness, and the disulfide bonds are broken at the present of glutathione. Anticancer drugs loaded on microgel can be released at tumor sites.

DESCRIPTION OF PREFERRED EMBODIMENTS

Figure 1:
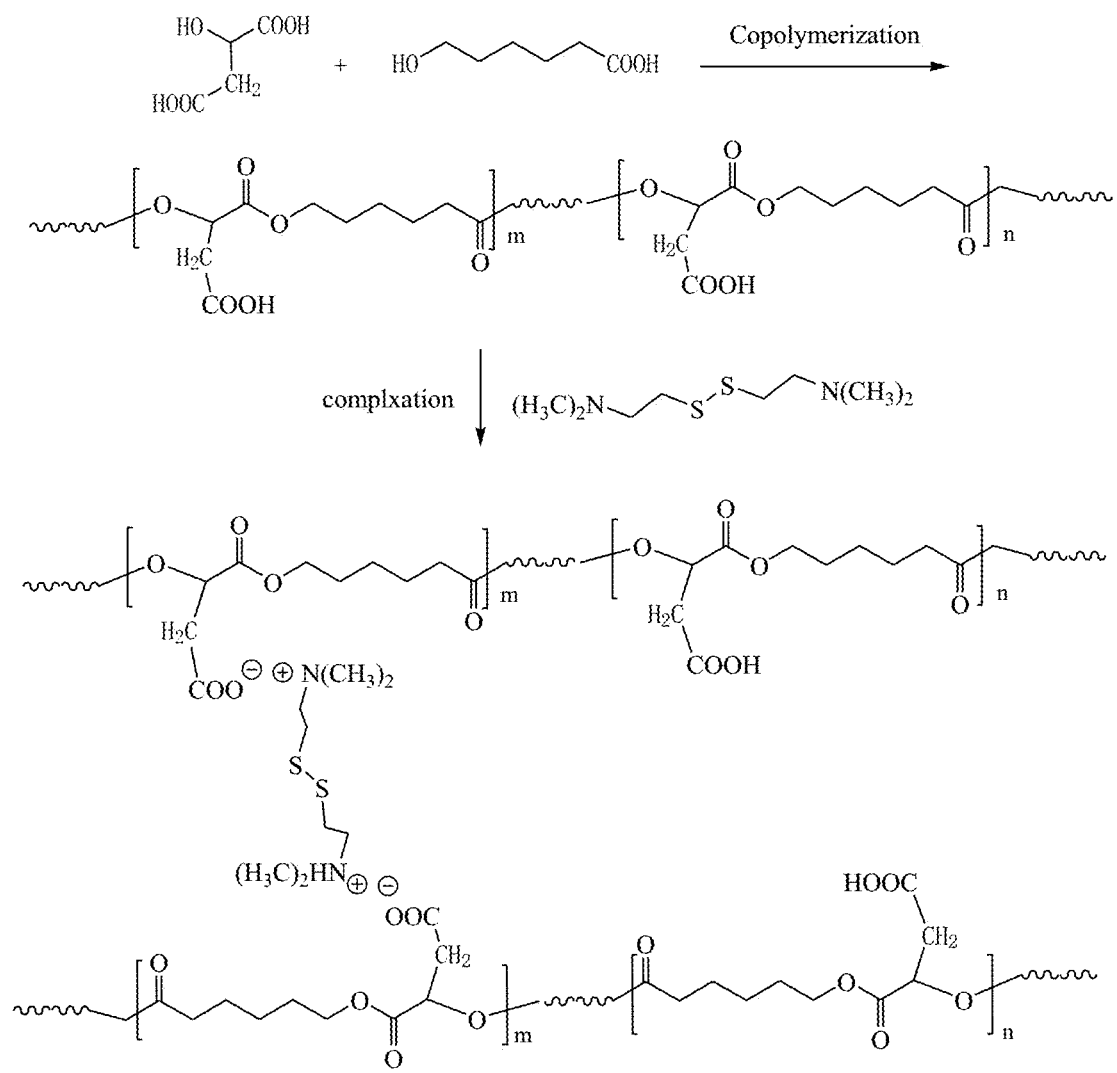
FIG. 1 is a schematic diagram of the synthesis of degradable and environmental responsive composite microgels in example 1.

The detailed implementation of the invention is further described as follows. The following embodiments are used to illustrate the invention, but not to limit the scope of the invention.

Example 1

The preparation of a degradable and environmental responsive composite microgel is presented as the follows:

Step 1: adding L-malic acid (Code: MA) 107.2 g and 6-hydroxyhexanoic acid (Code: HA) 13.2 g in a 250 ml three neck flask under stirring evenly, then adding p-toluenesulfonic acid 2.2 g to the flask, equipping a condenser tube and water separation device, putting the reaction flask in an oil bath for reaction 2 h at temperature of 85° C.; then, raising the temperature to 140° C. for continue reaction 12 h under reduced pressure (8-10 kpa) to obtain copolymers of L-malic acid and 6-hydroxyhexanoic acid, coded as PBH-1.

Step 2: mixing 22.5 g of cystamine hydrochloride, 100 ml of sodium hydroxide solution with 25 wt % of concentration and 20 ml of methanol, stirring at room temperature for 0.5 h, adding 56.8 g of iodomethane slowly under dark conditions, reacting at 25° C. for 9 h, extracting with an organic solvent, separating the organic layer, washing the organic layer by deionized water for three times, removing the organic solvent by vacuum distillation to obtain N,N,N',N'-tetramethyl cystamine;

Step 3: dissolving the copolymer (Code: PBH-1) in N,N-dimethylformamide to prepare a copolymer solution with 15 wt % of concentration; dissolving N,N,N',N'-tetramethyl cystamine in tetrahydrofuran to prepare N,N,N',N'-tetramethyl cystamine solution with 15 wt % of concentration; taking 8 ml of the copolymer solution and 1 ml of the N,N,N',N'-tetramethyl cystamine solution to mix, then slowly dropping the mixed solutions into 200 ml of distilled water under stirring for 8 h, transferring the mixture into a dialysis bag with cutoff molecular weight of 3500, dialysing against deionized water at room temperature for 72 h; changing the dialysate every 8 h; finally, a degradable and environmental responsive composite microgel is obtained after freeze-drying, coded as NMG-1.

Example 2

The preparation procedure is similar to example 1, excepting:

in Step 1, changing L-malic acid to 80.4 g, and the other operations are the same to example 1. The obtained copolymer of L-malic acid and 6-hydroxyhexanoic acid is coded as PBH-2;

in Step 3, changing the copolymer PBH-1 to PBH-2; changing 200 ml distilled water to 100 ml; the obtained degradable and environmental responsive composite microgel is coded as NMG-2.

Example 3

The preparation procedure is similar to example 1, excepting:

in Step 1, changing L-malic acid to 53.6 g, and the other operations are the same to example 1. The obtained copolymer of L-malic acid and 6-hydroxyhexanoic acid is coded as PBH-3;

in Step 3, changing the copolymer PBH-1 to PBH-3; changing 200 ml distilled water to 100 ml; the obtained degradable and environmental responsive composite microgel is coded as NMG-3.

Example 4

The preparation procedure is similar to example 1, excepting:

in Step 1, changing L-malic acid to 40.2 g, and the other operations are the same to example 1. The obtained copolymer of L-malic acid and 6-hydroxyhexanoic acid is coded as PBH-4;

in Step 3, changing the copolymer PBH-1 to PBH-4; changing 200 ml distilled water to 100 ml; the obtained degradable and environmental responsive composite microgel is coded as NMG-4.

Example 5

The preparation procedure is similar to example 1, excepting:

in Step 3, changing the volume of copolymer solution to 12 ml; the obtained degradable and environmental responsive composite microgel is coded as NMG-5.

Example 6

The preparation procedure is similar to example 1, excepting:

in Step 3, changing the volume of copolymer solution to 15 ml; the obtained degradable and environmental responsive composite microgel is coded as NMG-6.

Example 7

Preparation of the contrast copolymer: taking 40.2 g of L-malic acid and 9.0 g of L-lactic acid (Code: LA), adding them into a 250 ml three neck flask under stirring evenly, then adding 2.2 g of p-toluenesulfonic acid to the flask, connecting a condensation and water separation device; putting the reaction flask in an oil bath, raising the temperature to 85° C. for reaction 2 h, raising the temperature to 140° C. for further reaction 12 h under reduced pressure to 8-10 kpa, to obtain a copolymer of L-malic acid and L-lactic acid, coded as PBL.

Example 8

Figure 2:
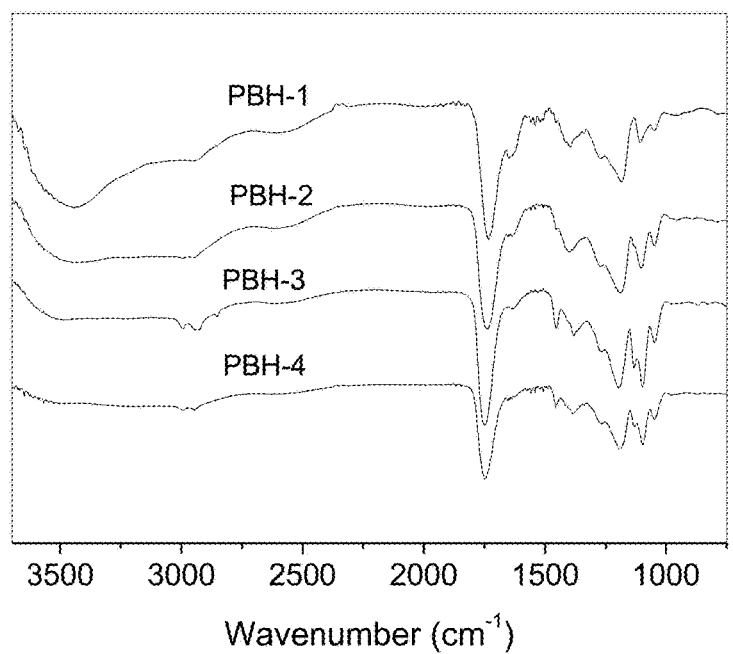
FIG. 2 is the infrared spectra of the copolymers of L-malic acid and 6-hydroxyhexanoic acid in example 1 to 4.

The infrared spectra of the copolymers of L-malic acid and 6-hydroxyhexanoic acid are determined on Fourier infrared spectrometer with scanning wavelength range of 4000-500 cm-1 and resolution of 4 cm-1. The results are shown in FIG. 2. It can be seen that the characteristic absorption peaks of the four copolymers are basically similar. The broad and scattered absorption peak at about 3500 cm-1 belongs to the stretching of —OH and —COOH; the small peak near 2950 cm-1 is the stretching of methylene in 6-hydroxyhexanoic acid; the stretching vibration peak at 1720 cm-1 is ascribed to C=O ester bond; the absorption peak at 950 cm-1 is the out of plane deformation vibration of OH . . . O, which can confirm the existence of side chain carboxyl group. The infrared spectra confirm the formation of the copolymers of L-malic acid and 6-hydroxyhexanoic acid.

Example 9

Figure 3:
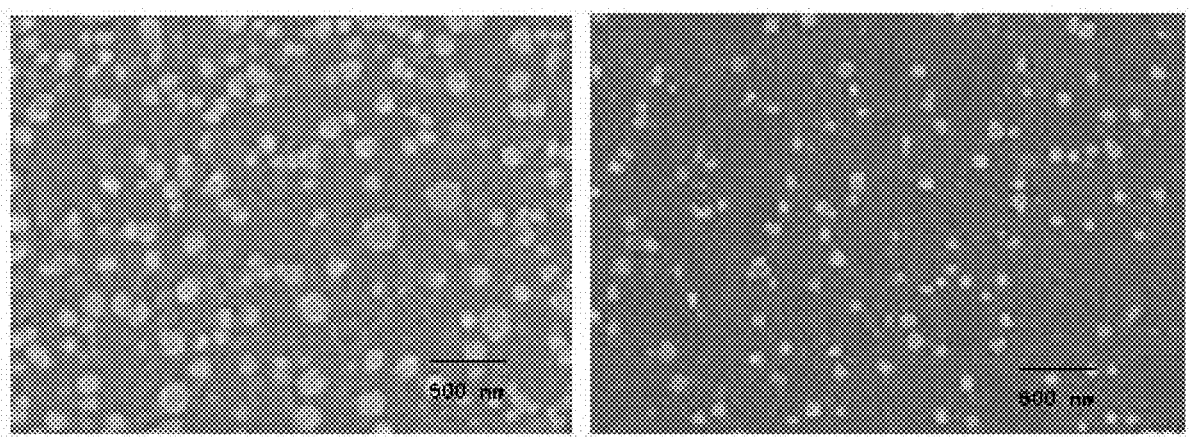
FIG. 3 is a scanning electron microscope photograph, a) NMG-1; b) NMG-4 of degradable and environmental responsive composite microgel; NMG-1 and NMG-4 are made in example 1 and example 4, respectively.

The microgel solution is dripped onto the silicon wafer and dried naturally, then gold is sprayed. The morphology of the composite microgel is observed under scanning electron microscope (S-4800 type of HITACHI Japan). FIG. 3 shows morphologies of NMG-1 and NMG-4, respectively. It can be seen that the prepared composite microgel are approximately spherical. When the molar ratio of L-malic acid to 6-hydroxyhexanoate is 8:1, the maximum diameter of the obtained microgel is around 280 nm. When the mole ratio of L-malic acid to 6-hydroxyhexanoate is 3:1, the diameter of the microgel is around 120 nm. This is because the free carboxyl group in the microgel decreases with the decrease of L-malic acid content in the copolymer, leading to decrease in swelling and the particle size.

Example 10

Figure 4:
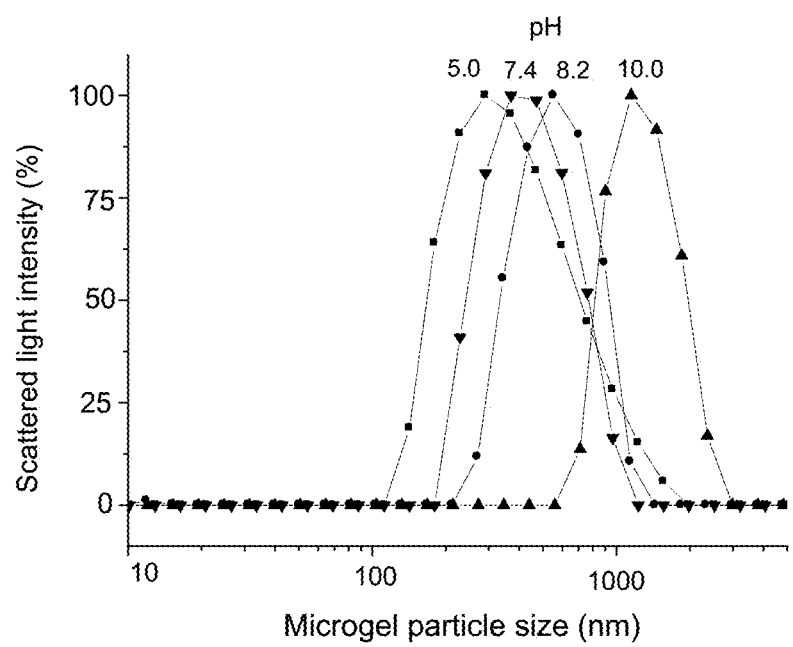
FIG. 4 shows the particle size change of degradable and environmental responsive composite microgel NMG-1 in example 1. under different acidic conditions.

The pH sensitivity of the composite microgels:

The microgel NMG-1 is placed in buffer solutions with different pH values, respectively, and the particle size change of the composite microgel is measured by laser light scattering instrument. The result is shown in FIG. 4. It can be found that the particle size of the composite microgel increases with the increase of pH in the solution. When pH=5.0, the particle size of the microgel is distributed around 230 nm. When the pH is increased to 10, the size of the microgel is about 1100 nm. Because there are free carboxyl groups in the microgel molecules, the COOH is changed to COO— under alkaline conditions, and the charge rejection effect results in the swelling of the microgels and the increase of particle size.

Example 11

Study on the degradation of copolymers: dissolving 2 g of the copolymers in 10 ml of N, N-dimethylformamide, adding deionized water 4 ml, staying at constant temperature 25° C., after different degradation time, 1 ml of solution is taken out. After measuring pH value, molecular weights of the copolymers are measured by gel permeation chromatograph. The results are shown in Table 1. It can be seen that with the increase of HA (6-hydroxyhexanoic acid) content in the feed, the molecular weight of the copolymer increases; at the same time, the degradation rate slows down, which is conducive to slow-release. In addition, compared with PBL the molecular weight of the copolymer of L-malic acid and L-lactate decreases more obviously in the same time, which indicates that the copolymer of MA and HA had a longer stable time in solution, and the acidity of the degradation product is decreased.

TABLE 1

Degradation results of copolymers of MA and HA

| copolymer Code | Molar ratio MA:HA | $\overline{M}_n$ at different degradation time | | | | pH (108 h) |
|---|---|---|---|---|---|---|
| | | 0 h | 36 h | 72 h | 108 h | |
| PBH-1 | 8:1 | 4100 | 3247 | 1595 | 638 | 3.8 |
| PBH-2 | 6:1 | 4670 | 3624 | 2017 | 710 | 4.1 |
| PBH-3 | 4:1 | 4720 | 4058 | 2347 | 784 | 4.6 |
| PBH-4 | 3:1 | 4890 | 4214 | 3185 | 2023 | 5.3 |
| PBL | 3:1 (LA) | 4150 | 1218 | 536 | | 2.1 |

Note:
MA is L-malic acid; HA is 6-hydroxycaproic acid; LA is lactic acid.
$\overline{M}_n$ is number average molecular weight.

Example 12

Preparation of drug loaded nano microgels: adding 50 mg of microgel powder from example 1 and 20 mg of doxorubicin hydrochloride to 100 ml of N, N-dimethylformamide, reacting at room temperature for 12 h, transferring to a dialysis bag with cutoff molecular weight of 3500, dialyzing for 8 h, to obtain drug loaded microgels after freeze drying.

Figure 5:
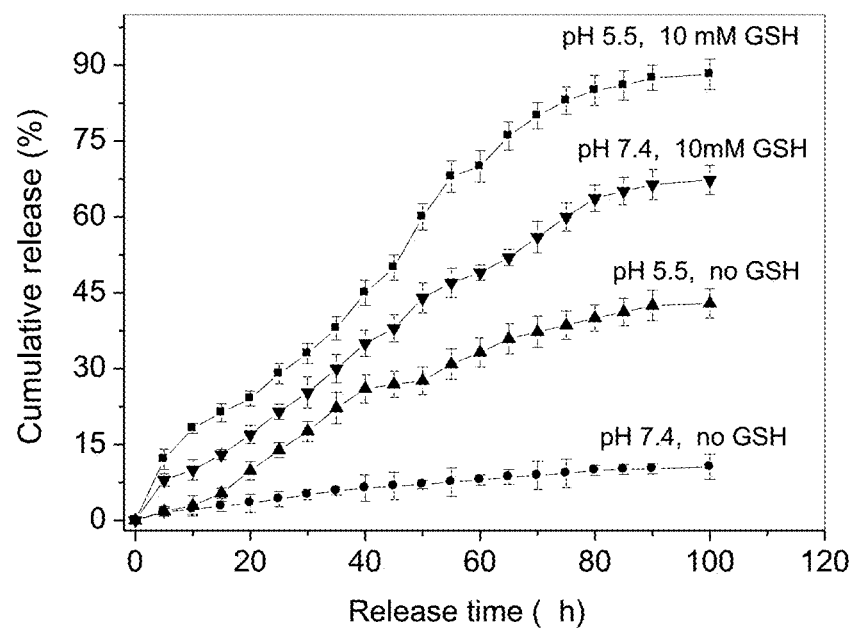
FIG. 5 is the control release of doxorubicin under different conditions for degradable and environmental responsive composite microgel NMG-1 which is made in example 1.

Drug release experiment: preparing drug loaded microgels solution with a concentration of 1 mg/ml by dissolving the dried microgels in deionized water; putting 2 ml of the solution into a dialysis bag and placing it in a 250 ml conical flask containing 20 ml of phosphoric acid buffer solution with different pH values and glutathione (GSH) concentrations at 37±0.5° C. Then, 3 ml of the solution is taken out at different time for determination of absorbance A483. The concentration of doxorubicin in the release medium is calculated from the standard curve, and the cumulative release curve is obtained and shown in FIG. 5.

Figure 6:
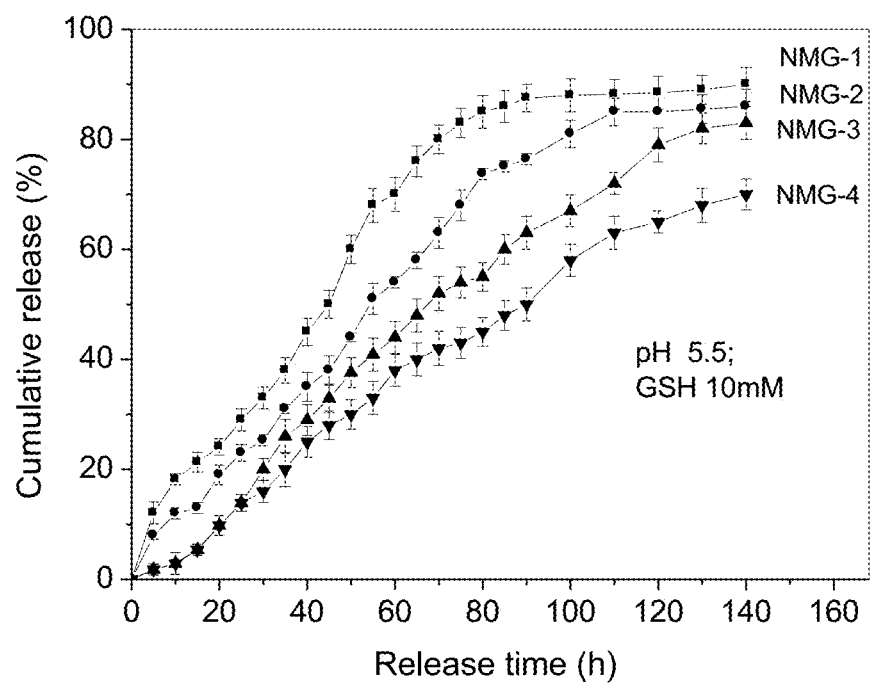
FIG. 6 shows the controlled release of doxorubicin under the same pH and GSH concentration using microgels of NMG-1, NMG-2, NMG-3 and NMG-4 which are made in example 1, example 2, example 3 and example 4, respectively.

It can be seen that under the same pH condition, the drug release in 10 mM GSH solution is faster than that in a solution without GSH. It is also observed that drug release in pH 5.5 buffer solution is faster than that in pH 7.4 buffer solution. The drug release has been studied using the microgels of NMG-1, NMG-2, NMG-3 and NMG-4 at the same pH and GSH concentrations, respectively. The results are shown in FIG. 6. It can be seen that from NMG-1 to NMG-4, the release rate slows down with the increase of HA content in composite microgels.

What is claimed is:

1. A method of preparing degradable and environment responsive composite microgels comprising:
   (1) reacting L-malic acid with 6-hydroxyhexanoic acid in the presence of a catalyst at a raised temperature to obtain a copolymer of L-malic acid and 6-hydroxyhexanoic acid;
   (2) mixing cystamine hydrochloride, sodium hydroxide solution and methanol, stirring, adding iodomethane slowly under dark conditions to effect reacting and obtain a reaction mixture, extracting the reaction mixture with an organic solvent, separating the organic layer, washing the layer by deionized water, removing the organic solvent by vacuum distillation to obtain N,N,N',N'-tetramethyl cystamine; and
   (3) dissolving the copolymer obtained from step (1) in N,N-dimethylformamide to prepare a copolymer solution; dissolving N,N,N',N'-tetramethyl cystamine from step (2) in tetrahydrofuran to prepare a N,N,N',N'-tetramethyl cystamine solution; mixing the copolymer solution with the N,N,N',N'-tetramethyl cystamine solution to obtain a mixed solution, then slowly dropping the mixed solution into water under stirring to obtain a mixture, dialyzing the mixture against deionized water; freeze-drying to obtain the degradable and environment responsive composite microgel.

2. The method of claim 1 wherein in step (1), the molar ratio of L-malic acid and 6-hydroxyhexanoic acid is 8:1~3:1.

3. The method of claim 1 wherein in step (1), the catalyst is p-toluenesulfonic acid which accounts for 1.8~4.2 wt % of the total mass of L-malic acid and 6-hydroxyhexanoic acid.

4. The method of claim 1 wherein in step (2), cystamine hydrochloride is 22.5 g, sodium hydroxide solution with 25 W % concentration is 100 mL, and methanol is 20 ml; the molar ratio of cystamine hydrochloride to iodomethane is 1:4.

5. The method of claim 1 wherein in step (2), the organic solvent is selected from the group consisting of trichloromethane, dichloromethane, ethyl acetate, ether, and combinations thereof.

6. The method of claim 1 wherein in step (3), the volume ratio of the copolymer solution to N,N,N',N'-tetramethyl cystamine solution is 8:1~15:1.

7. The method of claim 1 wherein in step (3), the volume of distilled water is 11~25 times of the total volume of the copolymer solution and N,N,N',N'-tetramethyl cystamine solution.

8. A method of making doxorubicin hydrochloride loaded microgels comprising reacting the degradable and environment responsive composite microgels made in claim 1 with doxorubicin hydrochloride in N,N-dimethylformamide to obtain a reaction mixture, dialyzing the reaction mixture against deionized water, then freeze-drying to obtain the doxorubicin hydrochloride loaded microgels.

* * * * *